United States Patent [19]

Moulton

[11] 4,186,378
[45] Jan. 29, 1980

[54] IDENTIFICATION SYSTEM

[75] Inventor: Clifford H. Moulton, Portland, Oreg.

[73] Assignee: Palmguard Inc., Beaverton, Oreg.

[21] Appl. No.: 817,623

[22] Filed: Jul. 21, 1977

[51] Int. Cl.² ............................................. G06K 9/12
[52] U.S. Cl. .................... 340/146.3 E; 340/146.3 MA
[58] Field of Search ............. 340/146.3 MA, 146.3 Q, 340/146.3 T, 146.3 E, 146.3 J, 146.3 AQ, 146.3 AE, 146.3 R, 149 R, 149 A

[56] References Cited

U.S. PATENT DOCUMENTS

| | | | |
|---|---|---|---|
| 3,292,149 | 12/1966 | Bourne | 340/146.3 E |
| 3,366,735 | 1/1968 | Hecker | 340/146.3 AE |
| 3,384,875 | 5/1968 | Bene et al. | 340/146.3 Q |
| 3,539,994 | 11/1970 | Clapper | 340/146.3 T |
| 3,576,534 | 4/1971 | Steinberger | 340/146.3 MA |
| 3,626,368 | 12/1971 | Lee | 340/146.3 T |
| 3,723,970 | 3/1973 | Stoller | 340/146.3 MA |
| 3,883,848 | 5/1975 | Minck et al. | 340/146.3 MA |
| 3,930,231 | 12/1975 | Henrichon, Jr. et al. | 340/146.3 MA |

Primary Examiner—Leo H. Boudreau
Attorney, Agent, or Firm—George T. Noe

[57] ABSTRACT

An identification system includes means for scanning an identity pattern in a predetermined manner and correlating previously-obtained recognition data with information derived therefrom to determine a positive identification. In obtaining recognition data, the identity pattern is scanned and digitized in a predetermined manner, and then analyzed and sorted to provide prominent information most likely to be recognized in subsequent identity verifications with the original recognition pattern. In this manner, unique recognition data for each identity pattern is stored and is available for rapid retrieval and correlation when the original identity pattern is presented.

12 Claims, 10 Drawing Figures

OUTPUT FOR "SINCH"

"INCH"

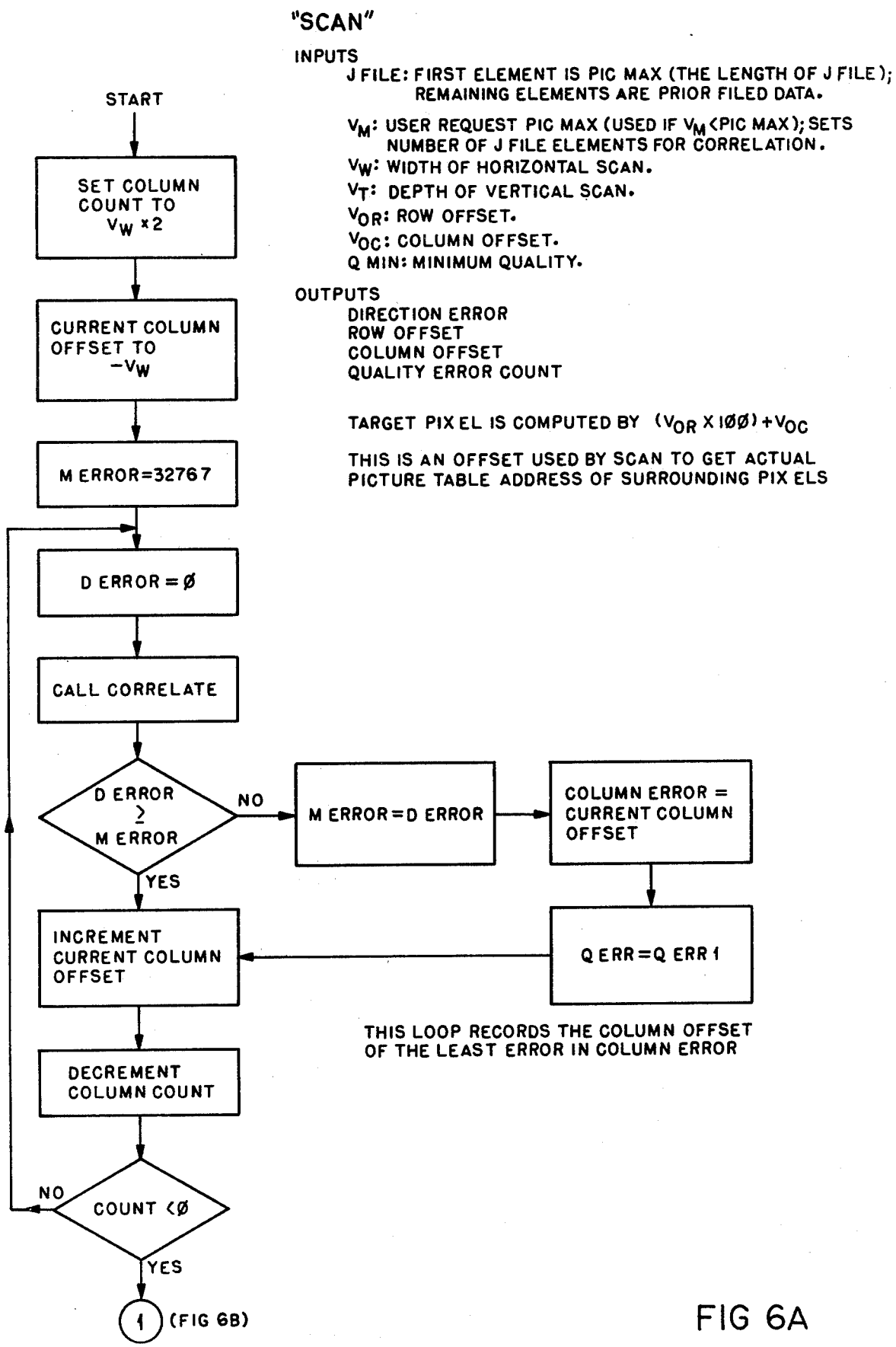

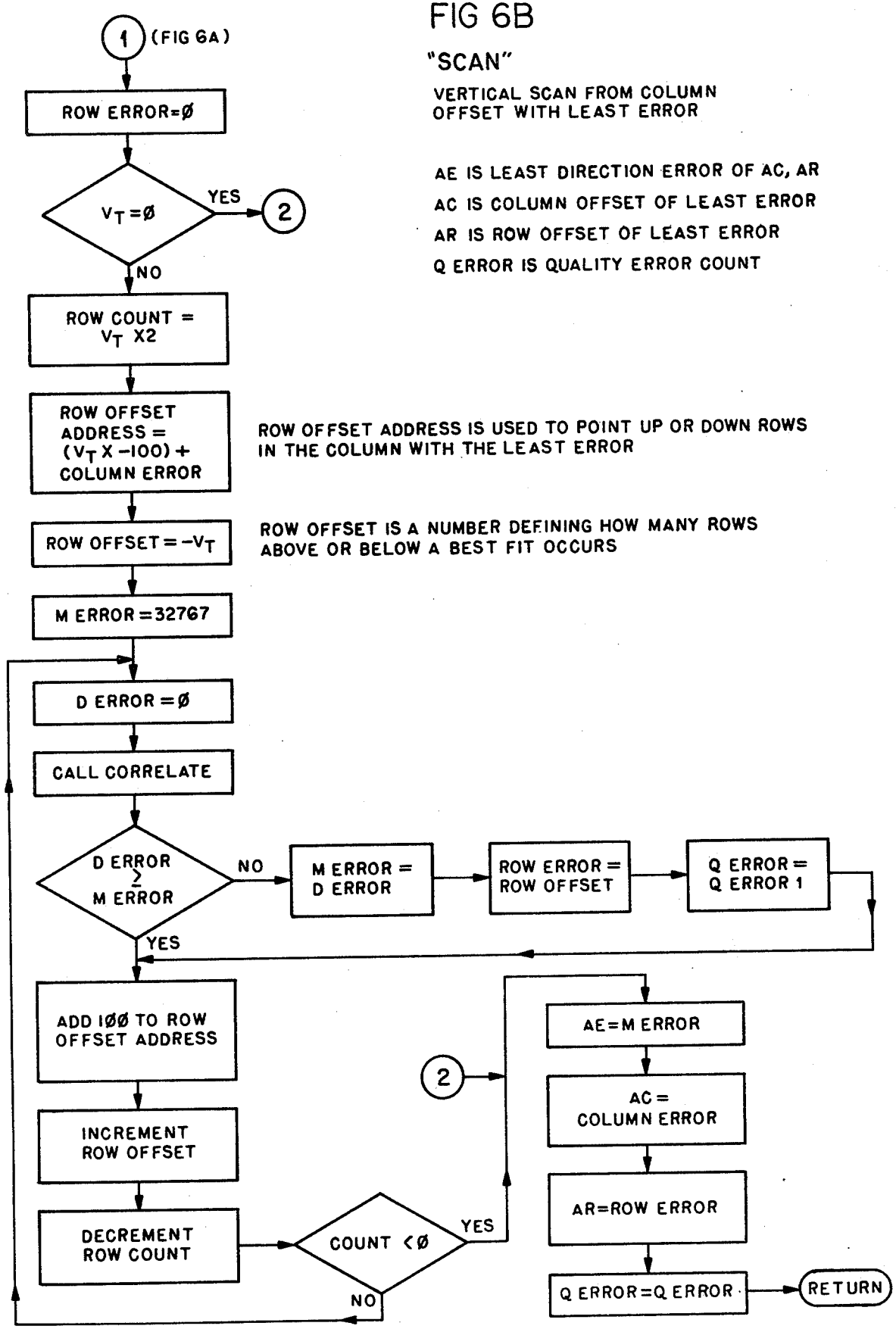

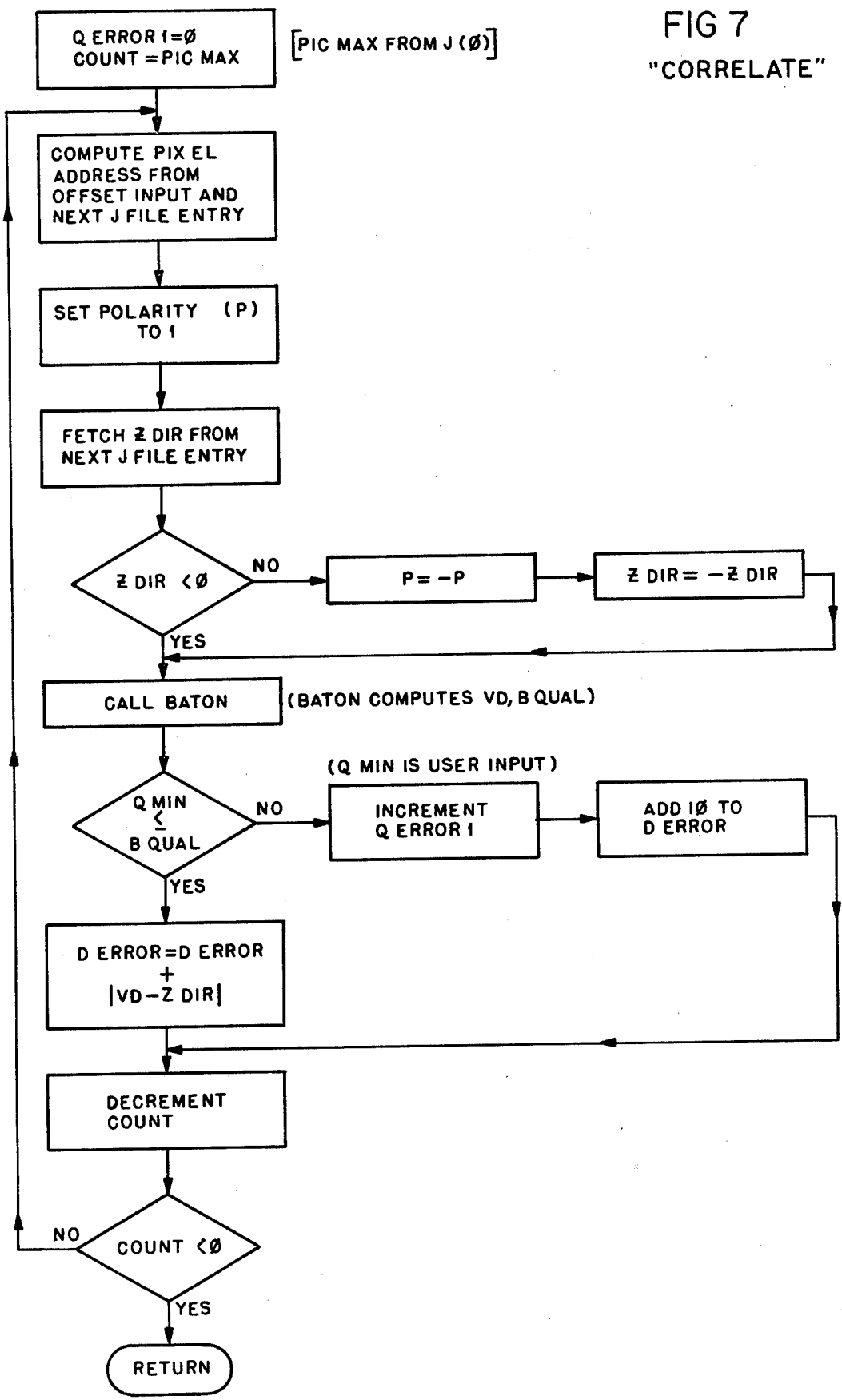

IDENTIFICATION SYSTEM

BACKGROUND OF THE INVENTION

Electronic identification systems are utilized in a number of applications where verification of identity is required, such as facilitating banking transactions and permitting access to restricted areas. Some of these systems merely read coded information magnetically stored on a plastic wallet-sized card, while more sophisticated systems are designed to provide a positive identification by reading an actual physical recognition pattern unique to an individual and comparing the data derived therefrom with previously stored data derived from the same pattern.

Because of the positive identification provided by fingerprints, a number of systems have been developed to scan fingertips with electromechanical means and derive recognition data relative to fingerprints. However, fingerprint identification devices have not attained popularity because of the reluctance on the part of the general public in having a record of their fingerprints permanently stored in a remote and inaccessible file, even though in most cases a code number relating to the fingerprint is stored away rather than the fingerprint itself.

It has been recognized that a palm print is unique, and at least one prior art identification system exemplified by U.S. Pat. No. 3,581,282 to Altman utilizes this information to provide recognitions data for proper identification.

One problem experienced by some prior art systems is that they attempt to verify identity with a one-to-one comparison of stored and new data, resulting in a high number of identification errors. Such errors can be those in which either a false recognition pattern is verified or a true pattern is rejected.

SUMMARY OF THE INVENTION

The present invention is related to identification systems in general, and in particular to an automatic electronic identification system for recognizing a pattern such as the palm print of a hand.

In developing recognition data, the palm of an individual's hand is scanned in a predetermined manner by a camera such as a vidicon or a solid state charge-coupled image sensor to produce an analog signal proportional to the light levels encountered as the ridges and valleys of the palm print are scanned. The analog signal is differentiated to enhance the ridges and valleys scanned, and thereby provide a greater selectivity of the pattern fragments. The enhanced analog signal is quantized by a conventional analog-to-digital converter to provide numerical digital data corresponding to the various light levels of the pattern fragments, and then this raw data is stored. Key information is then abstracted from the raw data to provide recognition data.

In a commercial embodiment of the present invention, the raw data is obtained by raster scanning and digitizing, and then storing the data in a 100×100 memory array to represent a complete picture of a palm identity pattern. The stored data may be analyzed line by line in a particular manner to develop data relating to the more prominent ridges or valleys, their directions in the palm pattern, and the locations or X-Y coordinates of these data in the pattern. These data may then be sorted and ranked in their order of most prominent to least prominent, and then stored in a separate array. Thus a predetermined number of the most prominent information details may be selected from the picture as recognition data and encoded in compact form for permanent storage. This recognition data abstracted from the raw data is available for rapid retrieval and correlation when the original palm is presented for identity verification.

For verification purposes, the palm pattern is read and stored in the same manner as the original raw data was obtained so that a correlation process can take place matching the compacted recognition data with raw data at substantially the same X-Y coordinates from which the recognition data was obtained. Based on this correlation, a decision is made as to whether the identity pattern is verified.

It is therefore one object of the present invention to provide an automatic electronic identification system employing a novel method of recognizing with a high degree of accuracy an identity pattern such as the palm of a hand.

It is another object to provide an identification system in which only a predetermined number of key recognition data of prominent pattern characteristics are stored.

It is a further object to provide an accurate identification system in which only key recognition data is correlated with an identity pattern submitted for recognition.

It is an additional object to provide a novel method for analyzing an identity pattern for recognition data, and sorting and ranking such data from most prominent to least prominent.

The subject matter of the present invention is particularly pointed out and distinctly claimed in the following description. The invention, however, both as to organization and method of operation together with further advantages and objectives thereof may best be understood by reference to the following description taken in conjunction with the accompanying drawings.

DRAWINGS

FIG. 1 is an overall block diagram of an identification system in accordance with the present invention;

FIGS. 2A and 2B together comprise a flow chart of the "SINCH" analysis process which may be performed by the recognition data analyzer portion of the system of FIG. 1;

FIGS. 3A through 3G are diagrams showing the pattern of picture elements evaluated to tetermine detail quality;

FIGS. 4A and 4B together comprise a complete flow chart of the "INCH" analysis process which may be performed by the recognition data analyzer portion of the system of FIG. 1;

FIG. 5 is a flow chart of the "BATON" analysis process;

FIGS. 6A and 6B comprise a flow chart of the "SCAN" test process; and

FIG. 7 is a flow chart of the "CORRELATE" test process.

DETAILED DESCRIPTION OF THE INVENTION

Figure 1:
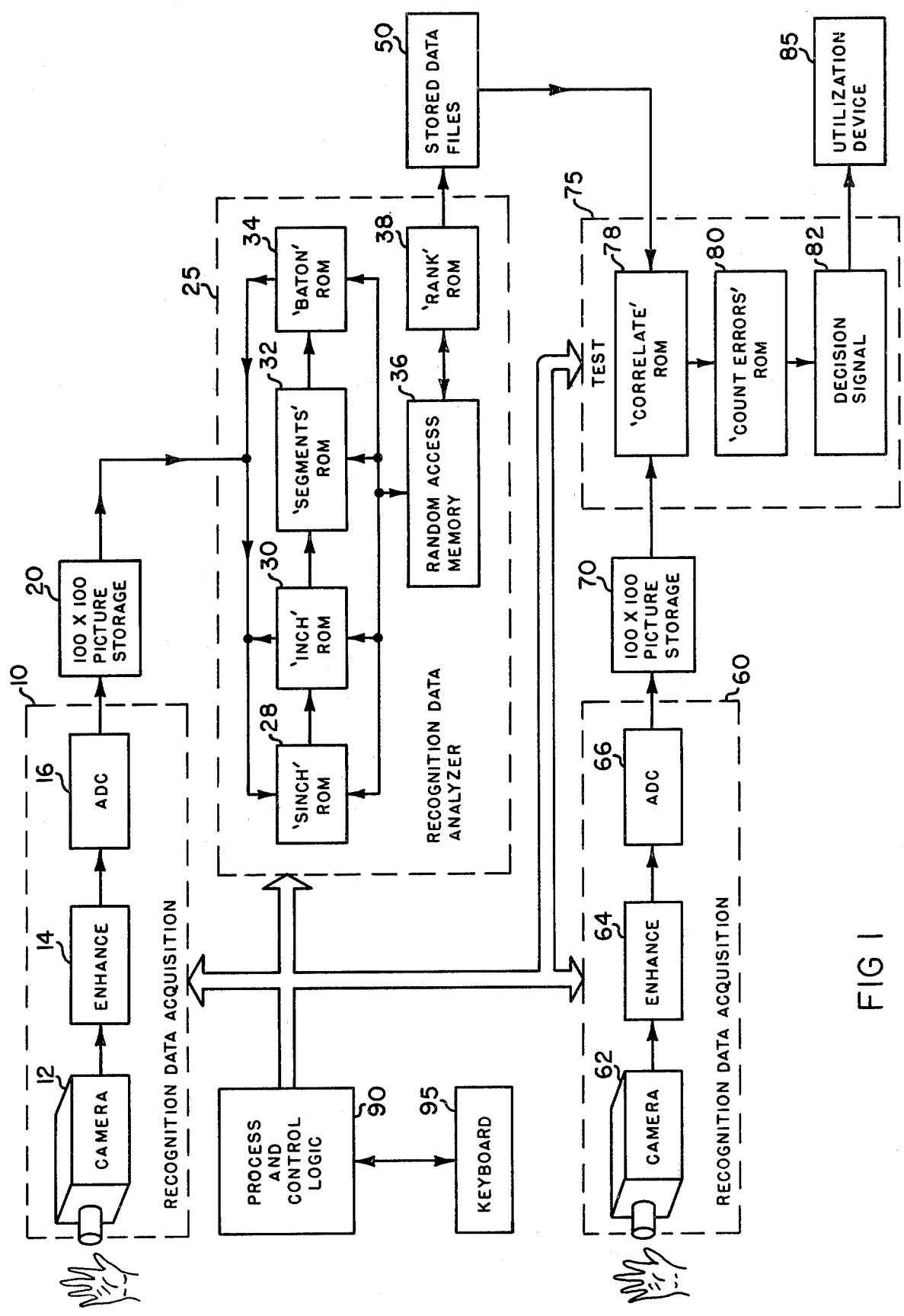

Referring now to FIG. 1, an overall block diagram of an entire identification system in accordance with a commercial embodiment of the present invention is shown. This particular system is designed to provide accurate personal identity verification by recognizing the ridge-and-valley pattern of the palm of a human hand, and is therefore optimized to provide this information.

Generally, the overall system comprises a recognition data acquisition unit 10, a storage unit 20, a recognition data analyzer 25, stored data files 50, a second recognition data acquisition unit 60, a second storage unit 70, a test unit 75, a utilization device 85, a process and control logic unit 90, and a keyboard 95.

A suitable jig device (not shown) may be provided for placement of the hand to ensure proper registration of the palm print for the initial recording of the recognition pattern by the acquisition unit 10 and each subsequent presentation of the palm for identity verification via the acquisition unit 60. A user's identity code number is assigned to each individual to be stored with his recognition data to facilitate retrieval thereof, and may also be utilized to set up the jig device for proper registration since hand sizes vary.

Recognition data acquisition unit 10 comprises a camera 12, an enhance circuit 14, and an analog-to-digital converter (ADC) 16. The camera suitably may be a television-type vidicon or a solid-state charge-coupled image sensor, such as a Fiarchild CCD 202. This camera raster-scans an image, outputting an analog voltage signal which corresponds to the light levels obtained from the image on each horizontal scan wherein a positive peak corresponds to a ridge in the palm pattern and a negative peak corresponds to a valley in the palm pattern. The enhance circuit 14 enhances the positive and negative peaks of the analog signal to provide a greater pronunciation of light and dark levels, and a conventional differentiating circuit such as a series capacitor and a shunt resistor will provide the desired enhancement. The enhanced analog signal is then quantized by the ADC 16 to provide numerical digital data which corresponds to the various voltage levels quantized. Many conventional analog-to-digital converters are available for this purpose.

The quantized or "digitized" signal is then stored line by line in a 10,000-element storage unit 20 such that essentially a 100-element by 100-element image of the palm pattern is stored. If this image were read out and viewed on an X-Y display device in the 100 by 100 format, it would be discerned that the vertically-oriented pattern components, or ridge and valley lines, are more prominent than the horizontally-oriented lines because of enhancement process which takes place as each horizontal line is recorded. Thus an optimized image is formed for the analysis and test processes which will be described later.

A recognition data analyzer 25 includes a number of read-only memories (ROM's) containing specific logic steps (program instructions burned in) for element-by-element analysis of the pattern image stored in the picture storage unit 20. These include SINCH ROM 28, INCH ROM 30, SEGMENTS ROM 32, and BATON ROM 34. A random access memory (RAM) 36 is connected to the ROM's 28, 30, 32, and 34 for temporary storage of data developed during the analysis process. Briefly, SINCH ROM 28 looks at each picture element in a horizontal row beginning with the bottom row to locate possible starting points to develop prominent pattern lines. The X-Y locations of possible starting points, which may be either positive or negative peaks, are temporarily stored in RAM 36. INCH ROM 30 then attempts to develop prominent pattern lines by looking generally upward into the picture to see if the peak information corresponding to a ridge or valley continues for a distance. The X-Y locations of these data are then inserted into arrays in the RAM 36. SEGMENTS ROM 32 breaks the arrays of data developed by the INCH ROM 30 into a number of segments which will best fit the expected information detail of the stored recognition pattern. BATON ROM 34 then tests each segment in order to determine those with the best information content to provide recognition data in the form of bidirectional vectors corresponding to key ridges and valleys of the palm pattern. The unsorted recognition data is inserted into an array in the RAM 36. At this point, the recognition data comprises the X-Y location of the center of each bidirectional vector, or baton, the vector direction, the quality factor depending upon nearby average light level, and the polarity. RANK ROM 38 contains a set of logic steps on program instructions for ranking the unsorted recognition data according to its quality so that recognition data relating to the most prominent details of the recognition pattern may be stored and used for subsequent verification of identity. The complete analysis process will be described in detail later.

It can be appreciated that the SINCH and INCH processes provide a methodical and orderly means for analyzing the picture information; however, either or both of these processes may be omitted to provide a less refined, faster analysis, which may in turn result in a reduced accuracy, depending upon the available picture details. For example, the system has been tested utilizing only the BATON process in a trial and error mode wherein in a predetermined pattern or number of picture elements are tested and recognition data abstracted therefrom. The analysis is thus performed more rapidly, but may miss important picture details. in a similar manner, either the SINCH or INCH processes may be utilized in conjunction with the BATON process to increase the probability of locating key recognition data. Up to a certain point, the certainty of an accurate identification is directly proportional to the number of key information data abstracted from the picture; and beyond that point additional abstracted data is not necessary.

Recognition data obtained by the recognition data analyzer 25 is stored along with the user's identity code number in data files 50. These data files suitably may be any storage medium intended for permanent storage, such as magnetic discs, tapes, cassettes, or cards. The data may be retrieved upon later command for identity verification.

The second recognition data acquisition unit 60 is utilized for identity verification. Camera 62, enhance circuit 64, and ADC 66 are identical to those described earlier in connection with recognition data acquisition unit 10. In fact, it should be pointed out that in some systems, the acquisition unit 10 may be utilized both for obtaining the original recognition data and for subsequent identity verification, precluding the need for a second acquisition unit 60. The same is true for picture storage unit 70, which is identical to picture storage unit 20.

For identity verification, the user punches his identification code number up on the keyboard 95. Conceivably, the keyboard 95 could be replaced with a card reader designed to read information from plastic wallet-sized card having a magnetic strip thereon, or, as a further alternative, a combination keyboard-card reader may be utilized. Additionally, the keyboard may include "prompting" lights or audible signals to guide the user through a series of steps. The user places his hand in the jig device mentioned earlier as the process and control logic unit 90 turns on the camera 62 to read the palm pattern. The process and control logic unit 90 suitably may be minicomputer or microprocessor hardware. Both have been successfully utilized in developing prototypes of the present invention, and the commercial embodiment employs a Zilog Z80 microprocessor. The enhanced palm pattern is stored line by line into the 10,000-element storage unit 70 in the same manner as described earlier in connection with storage unit 20.

The test unit 75 tests the recognition data stored in storage files 50 against the newly-obtained picture information in picture storage unit 70. The user's identity code number ensures retrieval of the correct data from the files. The test unit 75 includes a CORRELATE ROM 78, a COUNT ERRORS ROM 80, and a decision signal circuit 82. Briefly, CORRELATE ROM 78 includes a set of logic steps (program instructions) to determine the numerical agreement or degree of agreement with picture details taken from the same X-Y locations of the newly stored palm image in picture storage unit 70. Added steps may be incorporated to translate or skew or rotate the prior filed recognition data to match the new image details to correct for translational (X-Y displacement) or rotational registration errors. The COUNT ERRORS ROM 80 contains a set of logic steps (program instructions) to count errors each time recognition data from the files 50 differs from that in the picture storage unit 70 in various respects, with greater variances receiving a greater numerical error value. A running tally of the mismatch errors is applied to the decision signal circuit 82, for which one or more predetermined levels of decision are provided depending on the desired quality of correlation between the stored and new data. Decision signal circuit 82 suitably may comprise digital comparators or counters set to a predetermined count, or analog comparators having preset threshold levels. In either case, a decision is made thereby as to whether a reasonable match exists between the stored recognition data and the new recognition pattern, and an output signal is applied to a utilization device 85 indicating verification or rejection of the new recognition pattern. Thus, utilization device 85 suitably may include an electro-mechanical door-opening device, indicator lights, an alarm, etc. The complete test process will be described in detail later.

ANALYSIS PROCESS

For this discussion it will be assumed at all times that a complete image of a palm is stored in the 100-element by 100-element picture storage unit 20 as described hereinabove; that is, each element has stored thereon numerical data relating to a light level obtained from the palm print. If such data were read out and viewed on an X-Y display device, a picture of the palm print would be apparent, with the vertically-oriented lines being enhanced.

Figure 2A:
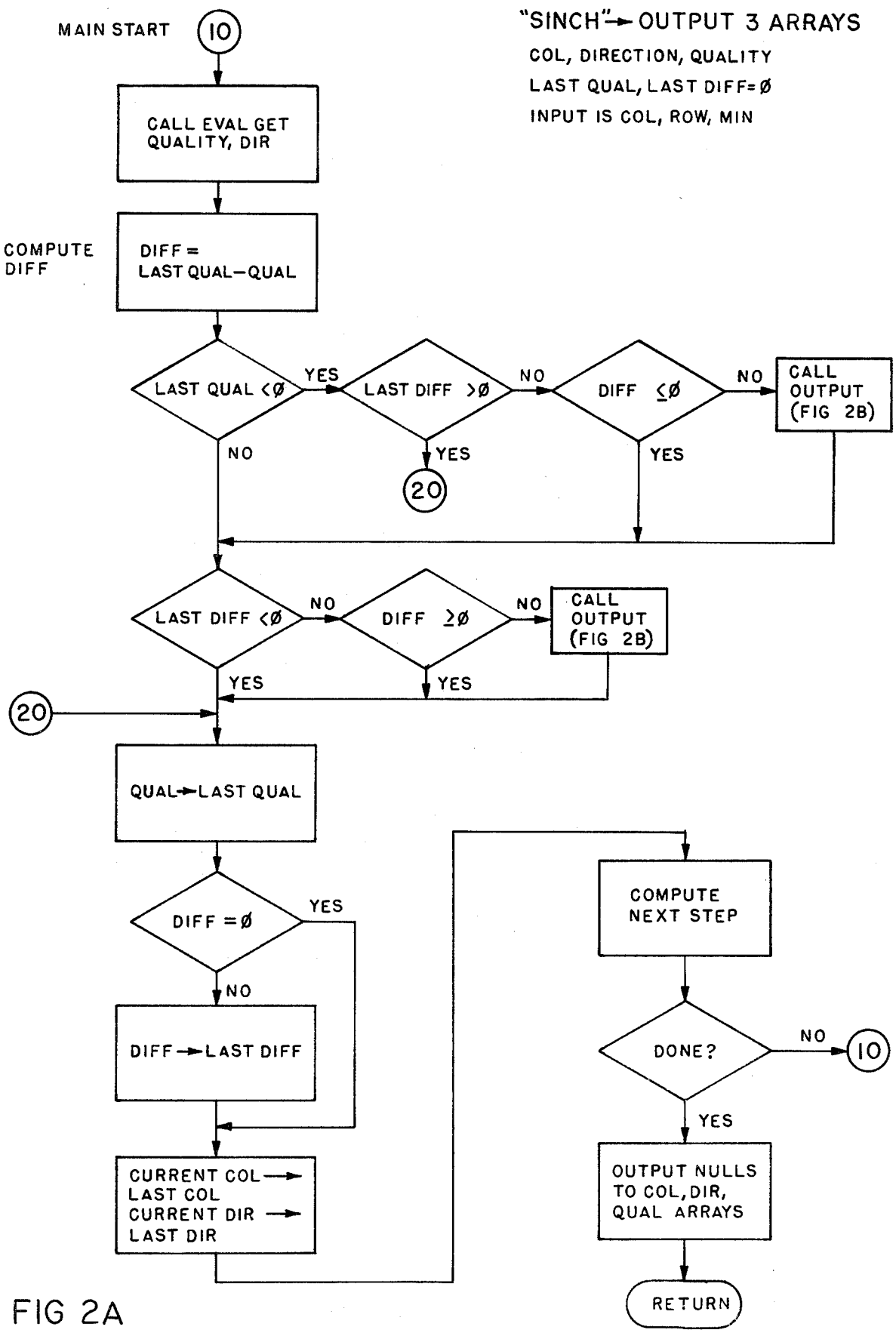
Figure 2B:
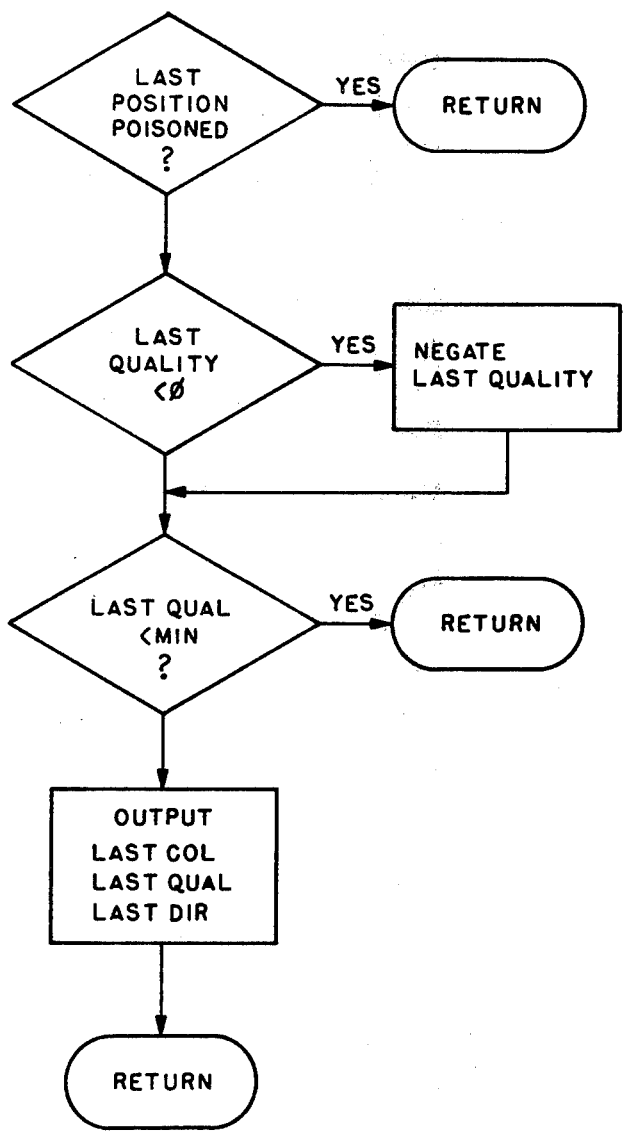
Figure 3:
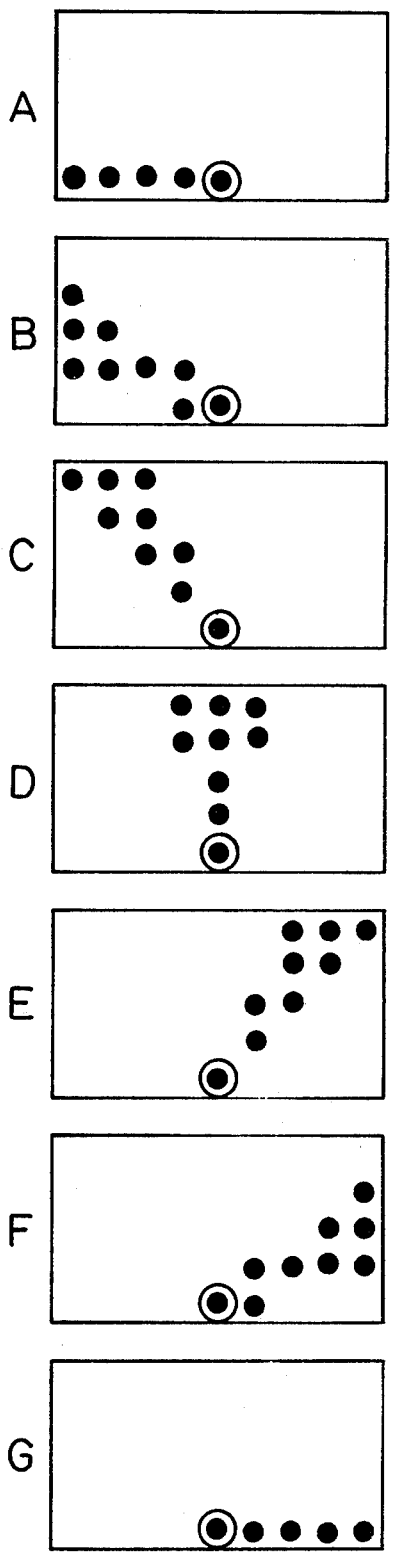

FIGS. 2A and 2B comprise a complete flow chart of the SINCH logic steps (program instructions) which are permanently stored in ROM 28. As mentioned previously, the SINCH ROM 28 looks at each picture element in a horizontal row beginning with the bottom row to locate possible starting points to develop the prominent enhanced vertically-oriented pattern lines. Rather than analyze just one element at a time and attempt to derive information therefrom, a 9×5 block of picture elements is analyzed wherein the bottom center element is the "home" element about which information is sought. Seven computations are made within the 9×5 block as shown in FIGS 3A–3G; the stored mathematical values of the 45 elements within the block are added up in the combinations shown. From these computations, five resulting measurements are developed to determine a line in one of the five directions depicted by FIGS. 3B–3F. Looking at FIG. 3D, for example, which indicates a line straight up, the total numerical value of the elements shown is tripled, and subtracted therefrom are the total numerical values of the elements of FIGS. 3C and 3E. This has a tendency to enhance the total value of the FIG. 3D computation if such value was originally greater than the adjacent total values. If the FIG. 3D direction is indeed a light line and the adjacent FIG. 3C and 3E directions are dark areas, not much would be subtracted, providing a strong output for the FIG. 3D measurement. On the other hand, if the FIG. 3D computation is equal to or less than the FIG. 3C and 3D computed values, the net result would be zero or negative. In this manner, one of the five directions depicted by FIGS. 3B, 3C, 3D, 3E, or 3F is selected as the stronger possibility of a line. The FIG. 3A and 3G elements are utilized in the computation of adjacent directions represented by FIGS. 3B and 3F respectively, and thus are not utilized as output possibilities. If the numerical output of the strongest evaluated measurement exceeds a predetermined value, it is said to have sufficient quality to be a starting point of a line. However, this information is not yet stored until the SINCH ROM 28 examines the next few adjacent home elements and their associated 9×5 block of elements in the same manner as just described. That is, SINCH progressively steps along the horizontal picture line inspecting each home element and its associated 9×5 block of elements for peak values, either positive or negative indicating respectively the start of either a light line or a dark line. The peak values having sufficient quality are stored together with the X-Y coordinate and predicted line direction, which may be represented by a number from 1 to 5, in an array in RAM 36 as possible starting points to be investigated by INCH ROM 30.

It might be mentioned that not every line or element need be evaluated by the SINCH ROM 28. For example, after SINCH ROM 28 locates all the starting possibilities along a line, INCH ROM 30 takes over and attempts to develop the lines. Once this step is completed. SINCH ROM 28 may skip one or more lines before looking for new possibilities. Additionally, once an element is developed as part of a line, the X-Y coordinate of the element is removed from further evaluation, or "poisoned," because it is already known that a line passes through that coordinate.

Figure 4A:
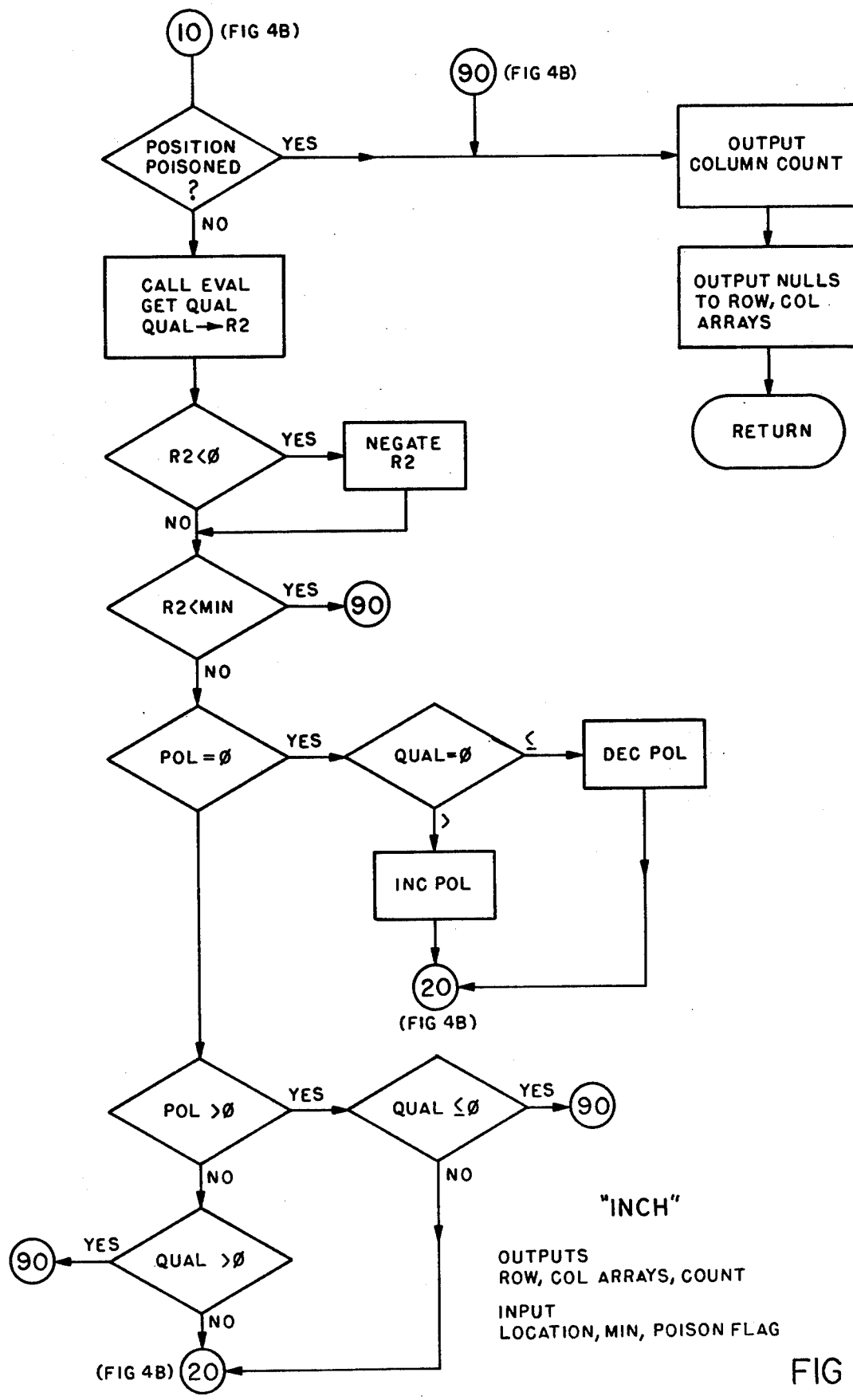
Figure 4B:
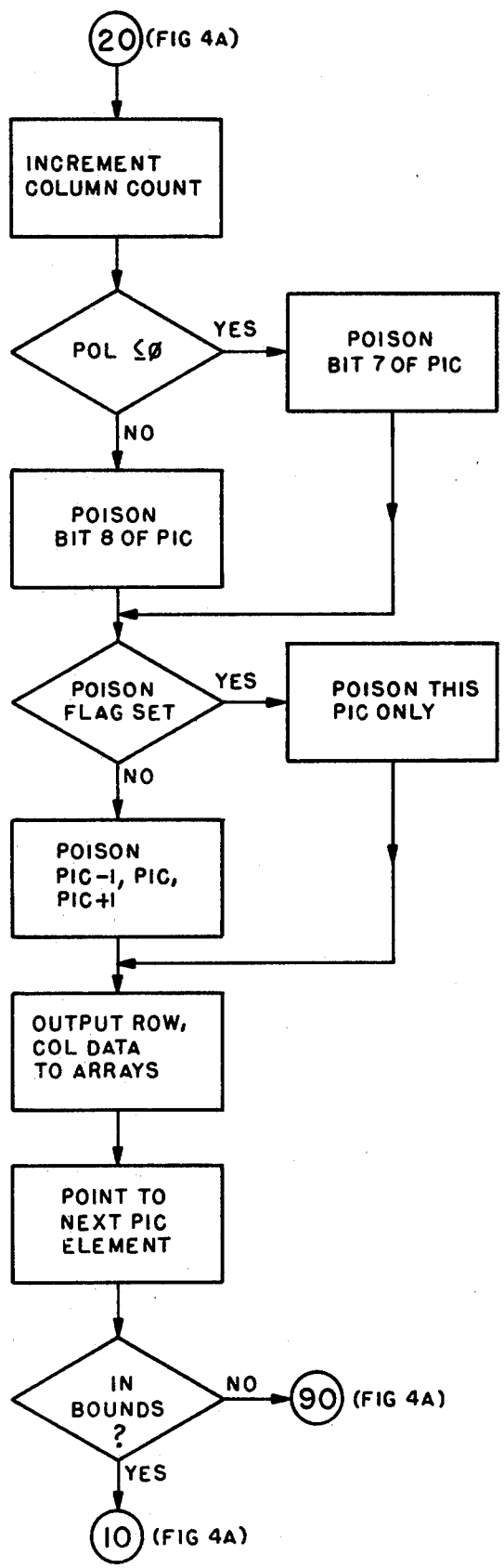

FIGS. 4A and 4B comprise a complete flow chart of the INCH logic steps (program instructions) which are permanently stored in INCH ROM 30. The INCH ROM 30 looks at the array of X-Y locations and associated information specified by SINCH ROM 28 and stored in RAM 36 as possible starting points to attempt to develop prominent palm pattern lines.

Beginning with the first possible starting point specified by SINCH ROM 28, the INCH ROM 30 looks generally upward into the picture to see if the peak information corresponding to a ridge or valley continues for a distance. This is achieved by an evaluation process similar to that described in connection with the SINCH ROM 28 and FIGS. 3A-3G. In fact, in the present embodiment, a set of logic steps called "EVAL" is shared by both the SINCH and INCH ROM's. The INCH process inches upwardly into the picture element by element in the direction specified by each preceding evaluation. Each home element and its associated 9×5 block of elements is examined to determine line quality and direction. Each accepted point of the newly-developed line, which accepted points include information as to X-Y location, direction, quality, and polarity, is stored in an array in the RAM 36. In stepping upwardly along the developing line, the horizontally adjacent element on either side of the predicted element is also tested to determine the best continuation of the line. Each nine contiguous accepted elements is stored in a separate array in RAM 36 by SEGMENTS ROM 32 to be acted on by the BATON procedure. As before, elements selected as acceptable line points are poisoned to preclude re-examination of already-accepted data.

There are three conditions upon which INCH will give up on the development of a particular line and go pick up a new staring point as specified by the SINCH ROM 28. These include insufficient quality level to maintain a clear line, reaching a picture border element, or reaching a poisoned element. When all of the starting possibilities on a horizontal line are exhausted, the SINCH ROM locates new starting points on a new row. Thus it can be discerned that the SINCH and INCH ROMS work together to develop the entire picture, starting from the bottom and working upwardly.

Figure 5:
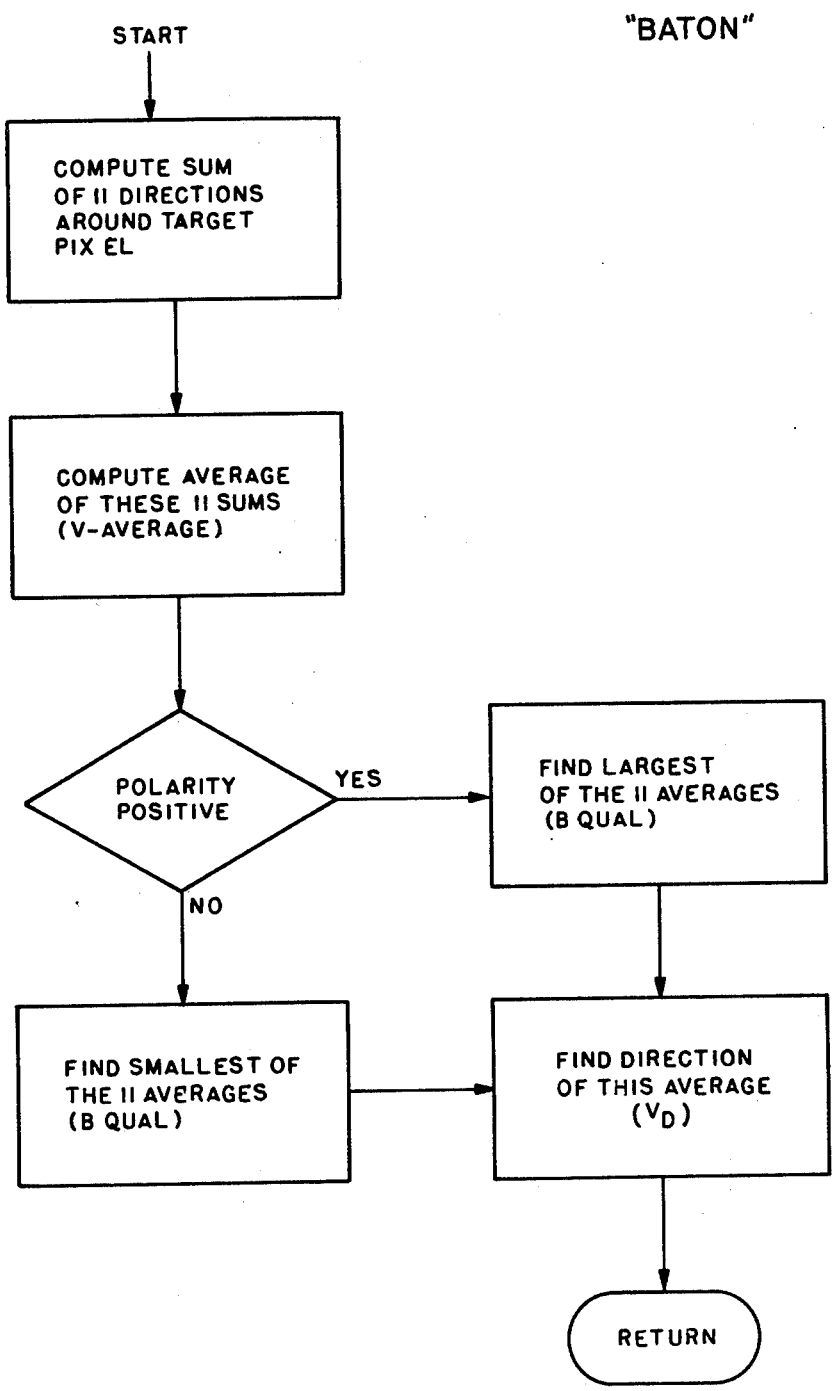

The next step in the analysis procedure is for the BATON ROM 34 to test each segment stored by the SEGMENTS ROM 32 in order to determine those with the best information content to provide recognition data which will best fit the expected information detail of the stored palm pattern in picture storage unit 20. A flow chart of the "BATON" process is shown in FIG. 5. BATON is directed to go to the center element of each nine-element line segment make a total of eleven evaluations about that point to analyze any possible line going through that point. In other words, the analysis involves pivoting about the point in eleven directions to make the determination, which analysis graphically would appear as the twirling of a baton. Additionally, BATON ROM 34 performs an adjust-for-fit procedure to determine the best baton location. This achieved by analyzing each horizontally-adjacent picture element to the segment center element chosen by SEGMENTS ROM 32 to see if a better fit can be obtained.

After BATON ROM 34 finds that the best line direction and fit of the line segments, the baton vectors are output into an array in RAM 36. The baton information includes the X-Y location of the center element of each baton or vector, direction (which is a number from one to eleven) quality, and polarity. While typically 100 or more batons might be abstracted from an image or palm pattern, a predetermined minimum number, which happens to be 49 in this embodiment, are needed to ensure a high degree of identification accuracy.

The unsorted baton vectors are next sorted according to quality by RANK ROM 38. All of the baton vectors in the array in RAM 36 are inspected, and a new array is developed therefrom. First RANK ROM 38 locates the baton vector having the highest quality in the first array, and stores the subscript of that array location in the first position in the second array. Then the second highest quality baton vector is chosen, and the subscript of that particular array location is stored in the second position in the second array, and so on. It can readily be seen that the baton vectors are ranked in proper sequence in the order of falling quality so that only the best are selected as recognition data. The ranking procedure terminates after 49 baton vectors are chosen since that is the number predetermined to achieve the degreee of accuracy of identification in this particular system.

The recognition data hereinabove obtained is encoded and stored in the output data files 50 along with the user's identification number. This completes the analysis process of the recognition data analyzer 25.

TEST PROCESS

For this description, it will be assumed that recognition data relating to the palm pattern of a particular individual is stored in the data files 50, and a new picture has been acquired by acquisition unit 60 and stored in picture storage unit 70. Upon entry of the user's identity code, for example, either by pushing buttons or inserting a magnetized card, process and control logic unit 90 retrieves the recognition data from the data files 50 for testing by the test unit 75.

FIGS. 6A and 6B comprise a complete flow chart of a test procedure called "SCAN." FIG. 7 comprises a flow chart of the CORRELATE logic steps (program instructions) which are permanently stored in CORRELATE ROM 78. Additionally, "Correlate" may call "BATON" previously described in connection with FIG. 5. As mentioned previously, the correlate procedure tests the file of X-Y locations and related characteristics of the stored baton vector recognition data against data at the same X-Y locations in the new picture to determine the numerical agreement, or degree of agreement between the stored and new data. For example, each X-Y location of the stored 49 baton vectors is sequentially inspected in the new picture to determine whether or not the same baton vector could be abstracted from the new picture. To minimize the error count, the CORRELATE procedure moves the test locations about to find the best fit location of registration between the prior files and the new image. That is, an X-Y location is first tested for the expected correlation. Error counts having predetermined weights or values are made when the tested direction and quality differ from the recognition data. An error tally is made at the tested X-Y location, then tests are made on adjacent picture elements in first the vertical and then the horizontal directions to determine the point of minimum error count. At the point of minimum error count, and of course zero errors indicates a perfect data match, the picture is in registration and the remaining recognition data locations may be checked.

In the process of checking the expected data locations, certain procedures from the recognition data analyzer unit 25, such as BATON and the quality evaluation processes, may be called upon to obtain matching data.

A second refinement for registration involves rotating or skewing the prior location data by the CORRELATE ROM 78 to minimize rotational registration errors.

The COUNT ERRORS ROM 80 maintains a running tally of the discrepancies between the prior files and the new image. Greater variances between the prior files and the new data receive a greater numerical error.

These variances include both direction and quality, and the degree to which they vary determines the numerical error assigned to the mismatch. For example, the BATON process includes eleven directional evaluations as mentioned earlier, and each baton vector abstracted from the original picture receives a number from one to eleven in accordance with its particular direction. Thus if CORRELATE ROM 78 is checking a particular X-Y location on the new picture and determines the vector direction to be nine when a seven is expected, the error is the numerical difference, or two.

The running tally of mismatch errors is applied to the decision signal circuit 82 which makes an identity verification decision based on the number of errors counted.

SUMMARY

In summary, an identification system has been shown and described in which an identity pattern is scanned and digitized in a predetermined manner, and then analyzed to abstract key recognition data therefrom. The recognition data may be ranked in accordance with the prominence of picture details abstracted, and stored in information files for subsequent identity vertification. A correlation between the prior stored files and new picture information is made, analyzing the new picture details with some of same analysis processes utilized in obtaining the stored data. An error count is made of the mismatches between the old and new data, and a recognition decision is made based thereon.

It will, therefore, be appreciated that the aforementioned and other desireable objects have been achieved; however, it should be noted that the particular embodiment which is shown and described herein, is intended as merely illustrative and not restrictive of the invention.

The invention is claimed in accordance with the following:

1. A method of providing identification of a person by the characteristics of his palm, comprising the steps of:
    scanning by opto-electronic means the palm of said person and producing an analog signal proportional to levels of light of said palm;
    converting said analog signal to digital picture data representative of a substantially complete picture of said palm;
    storing said digital picture data in a picture storage device;
    electronically analyzing said picture data and selecting therefrom recognition data corresponding to prominent characteristics of said recognition pattern, said recognition data including point location, line quality, and line direction of pattern lines of said palm; and
    storing said recognition data to provide said identification.

2. A method in accordance with claim 1 further including the step of passing said analog signal through a differentiating network to enhance details of said recognition data.

3. A method in accordance with claim 1 wherein said step of analyzing said picture data further includes ranking said recognition data in order from highest quality to lowest quality in accordance with the prominence of characteristics of said palm.

4. A method in accordance with claim 1 further including the steps of testing said stored recognition data with new picture data to determine a correlation therebetween, counting correlation mismatch errors, and providing a decision signal to a utilization device.

5. An apparatus for identification of a recognition pattern, comprising:
    means for scanning an object having a recognition pattern thereon and producing an analog signal proportional to levels of light of the scanned object;
    means for converting said analog signal to digital picture data representative of a substantially complete picture of said recognition pattern;
    first storage means for storing said digital picture data in storage locations representative of graphic point locations of said picture;
    analyzer means coupled to said first storage means for analyzing said picture data and selecting therefrom recognition data corresponding to prominent characteristics of said recognition pattern, said recognition data including point location, line quality, and line direction of pattern lines; and
    second storage means for storing said recognition data to provide said identification.

6. An apparatus in accordance with claim 5 further including an enhance circuit interposed between said scanning means and said converting means, said enhance circuit comprising a differentiating network.

7. An apparatus in accordance with claim 5 wherein said first storage means comprises a picture storage array having picture elements corresponding to said graphic point locations of said picture; and said analyzer means includes means for sequentially inspecting said picture elements to determine starting points for developing pattern lines, and further includes means for evaluating a plurality of contiguous picture elements to develop said pattern lines.

8. An apparatus in accordance with claim 7 wherein said analyzer means further includes means for ranking said recognition data in order of prominence of details from highest quality to lowest quality.

9. An apparatus in accordance with claim 7 wherein said analyzer means comprises a plurality of read-only memories containing program steps, and at least one random-access memory.

10. An apparatus in accordance with claim 5 further including test means for testing said recognition data stored in said second storage means with new picture data to determine a correlation therebetween, and utilization means responsive to said correlation for indicating verification or rejection of said identification.

11. An apparatus in accordance with claim 10 wherein said test means comprises a plurality of read-only memories containing program steps for determining the correlation between said recognition and said picture data and for counting correlation mismatch errors, said test means further comprising decision circuit means responsive to said correlation and said mismatch errors for making an identification decision.

12. An apparatus in accordance with claim 10 further including process and control logic means coupled to said scanning means, said analyzer means, and said test means for controlling the operating sequence thereof.

* * * * *